United States Patent [19]

Jullien

[11] Patent Number: 5,080,651
[45] Date of Patent: Jan. 14, 1992

[54] COMBINED PROTECTIVE GUARD AND DESTRUCTION SYSTEM FOR A SYRINGE

[76] Inventor: Robert G. Jullien, 2904 Graham Rd., Falls Church, Va. 22042

[21] Appl. No.: 661,243

[22] Filed: Feb. 27, 1991

Related U.S. Application Data

[63] Continuation-in-part of Ser. No. 360,585, Jun. 2, 1989.

[51] Int. Cl.$^5$ .............................................. A61M 5/00
[52] U.S. Cl. ...................................... 604/110; 206/365
[58] Field of Search ............... 604/110, 111, 187, 192, 604/198, 263; 206/364, 365, 366

[56] References Cited

U.S. PATENT DOCUMENTS

| | | | |
|---|---|---|---|
| 4,266,544 | 5/1981 | Wardlaw | 604/110 |
| 4,332,323 | 6/1982 | Reenstierna | 206/365 |
| 4,634,428 | 1/1987 | Cuu | 604/110 |
| 4,802,579 | 2/1989 | Hall et al. | 206/366 |

FOREIGN PATENT DOCUMENTS

| | | | |
|---|---|---|---|
| 3012646 | 10/1981 | Fed. Rep. of Germany | 604/110 |
| 2201094 | 8/1988 | United Kingdom | 604/110 |
| 9000070 | 11/1990 | World Int. Prop. O. | 604/110 |

*Primary Examiner*—John D. Yasko
*Attorney, Agent, or Firm*—Longacre & White

[57] ABSTRACT

The invention provides, in combination, a guard tube for surrounding and protecting a needle of a syringe, the barrel of the syringe being slidable within the guard between an extended position in which the needle is enclosed by and sealed within the guard and a retracted position in which the needle either protrudes from the guard through an aperture in an end-piece or is destructively crushed against the blocked off end-piece as the syringe barrel is forcibly slid into that retracted position, and a crush tube in the form of a tubular receptacle closed at one end in which the forward end of the syringe-guard assembly is placed prior to the destruction step. The crush tube may include a disposable liner, in order to completely isolate the assembly during the crushing of the needle and to enable the assembly to be easily and safely disposed of, without risk of leakage of contaminants.

15 Claims, 17 Drawing Sheets

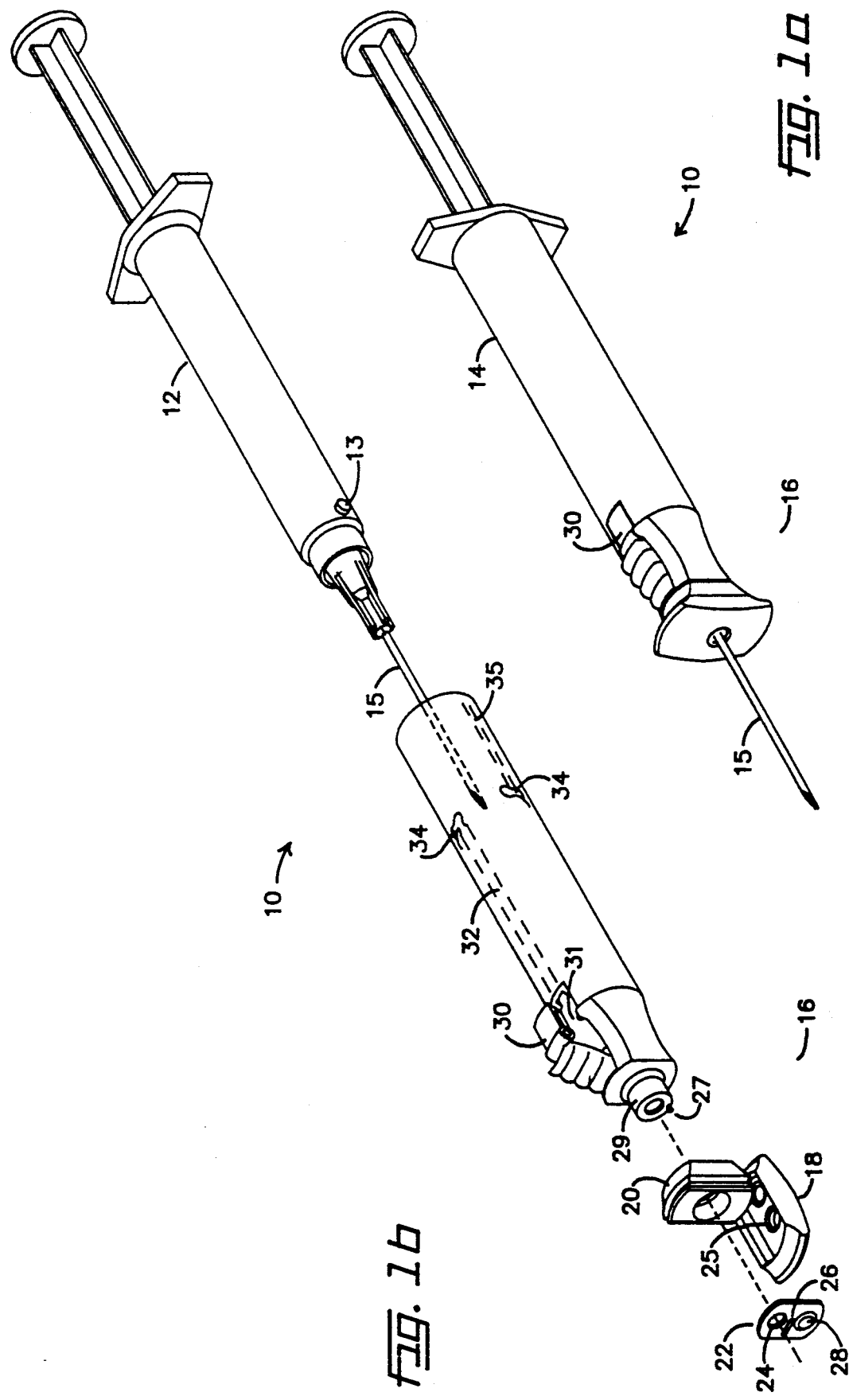

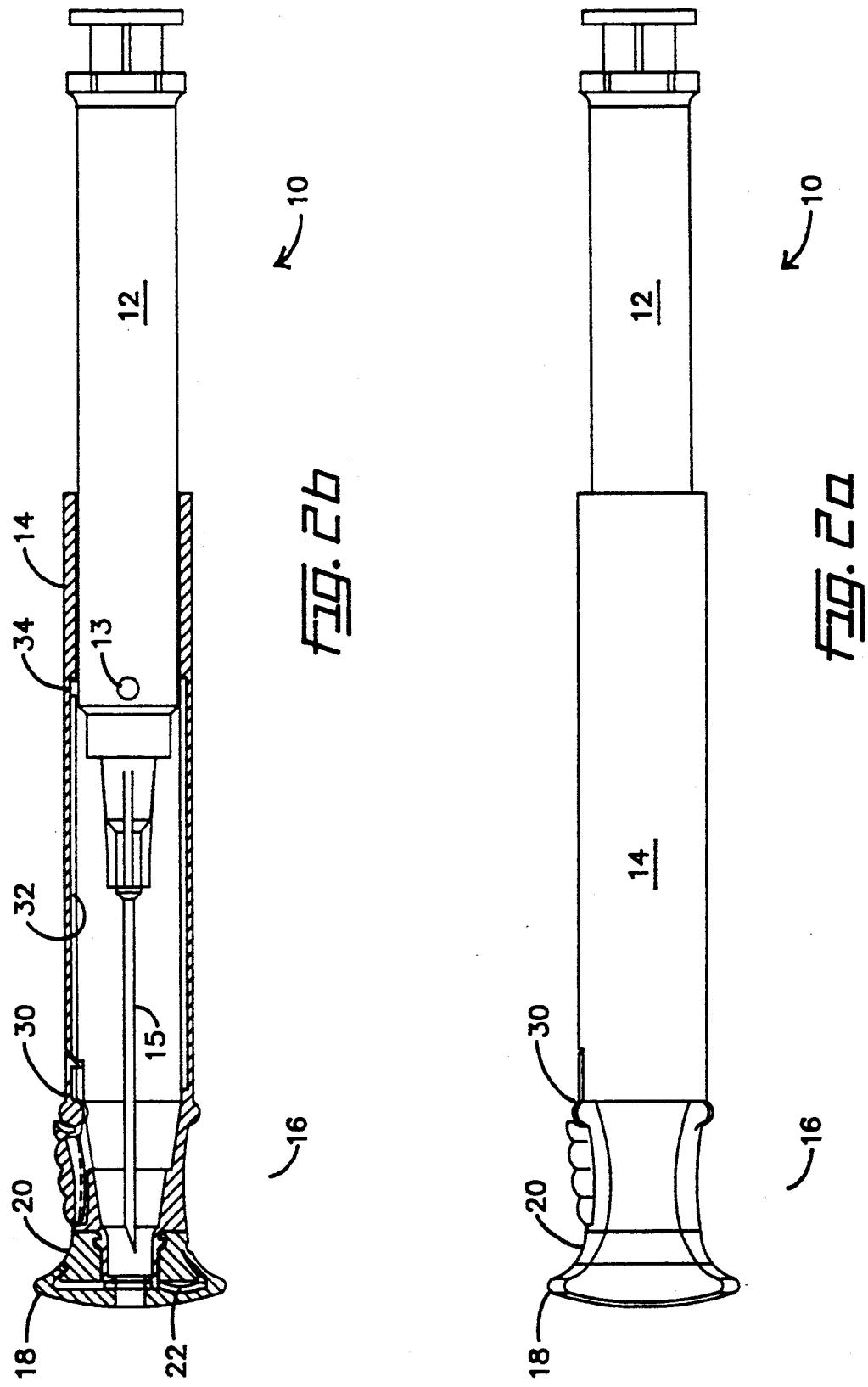

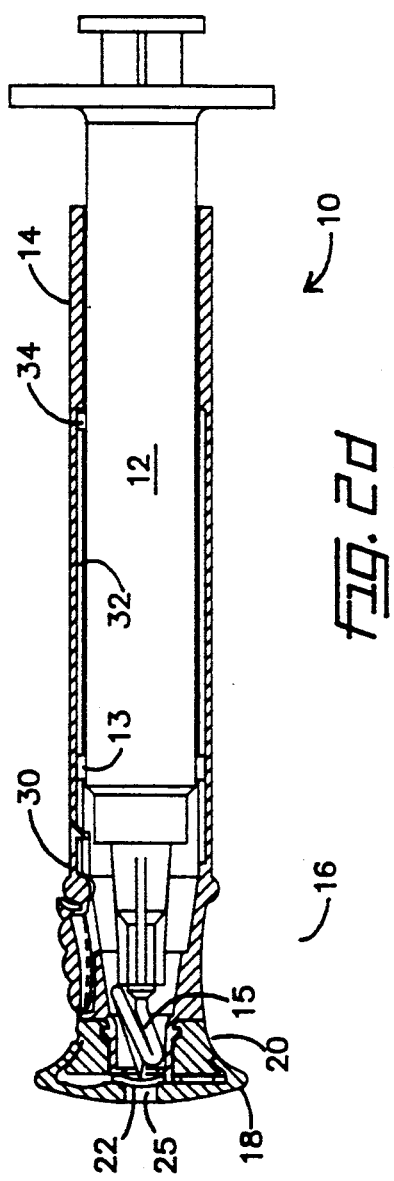
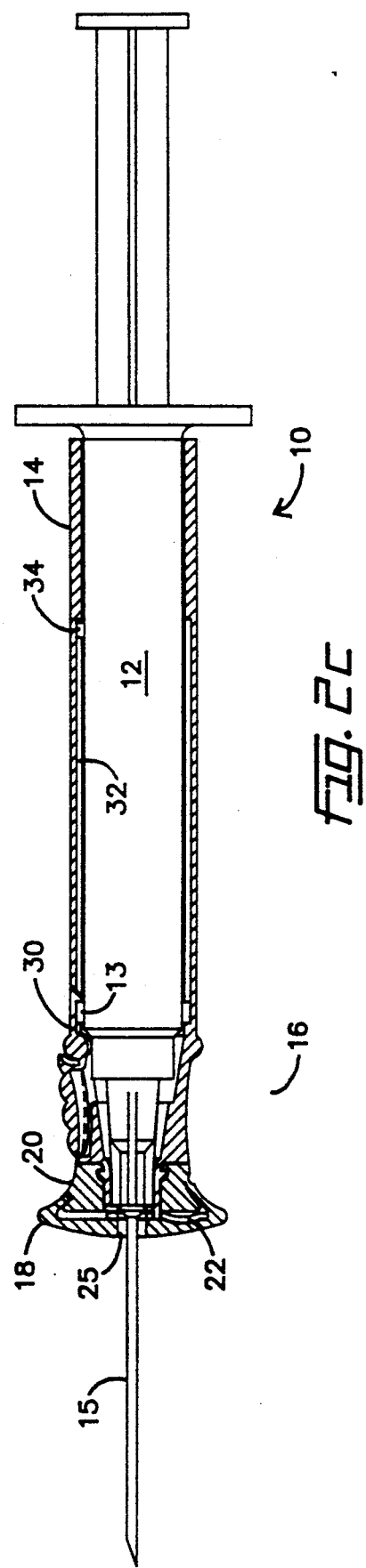

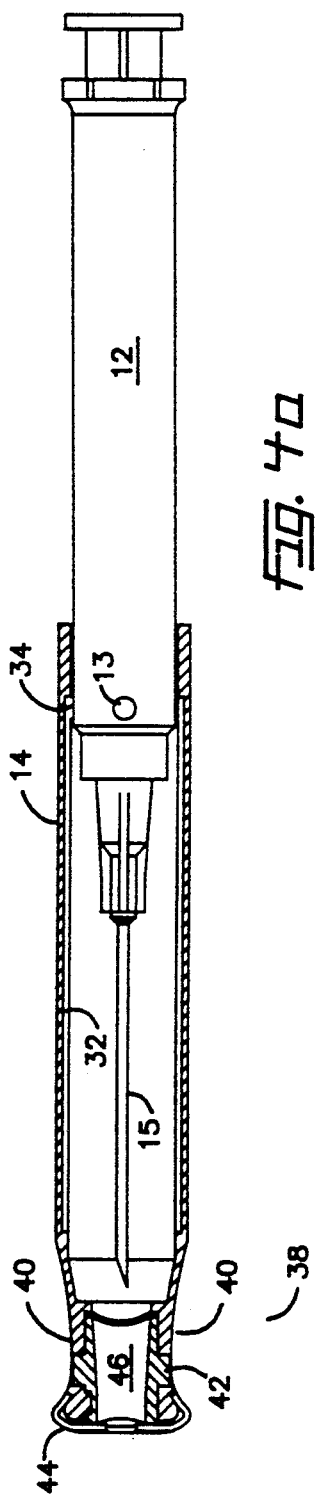
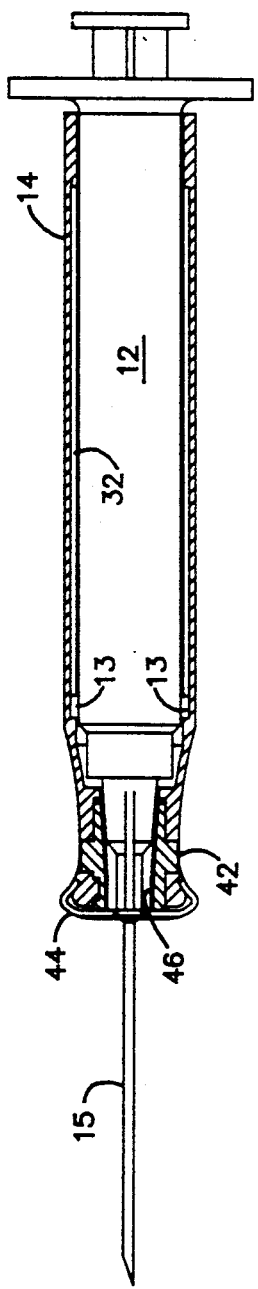
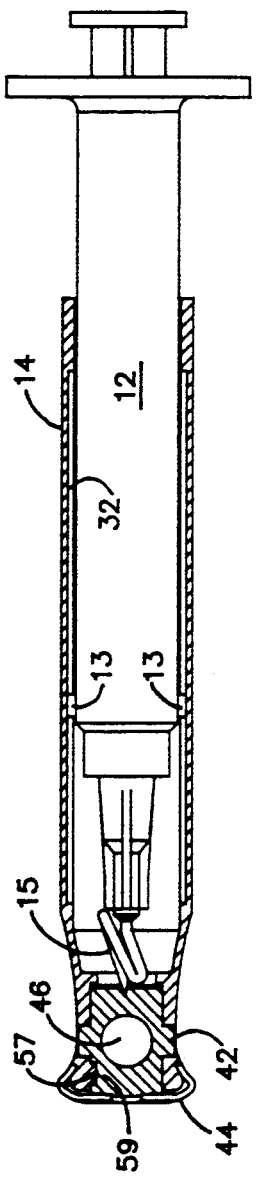
Fig. 4a
Fig. 4b
Fig. 4c

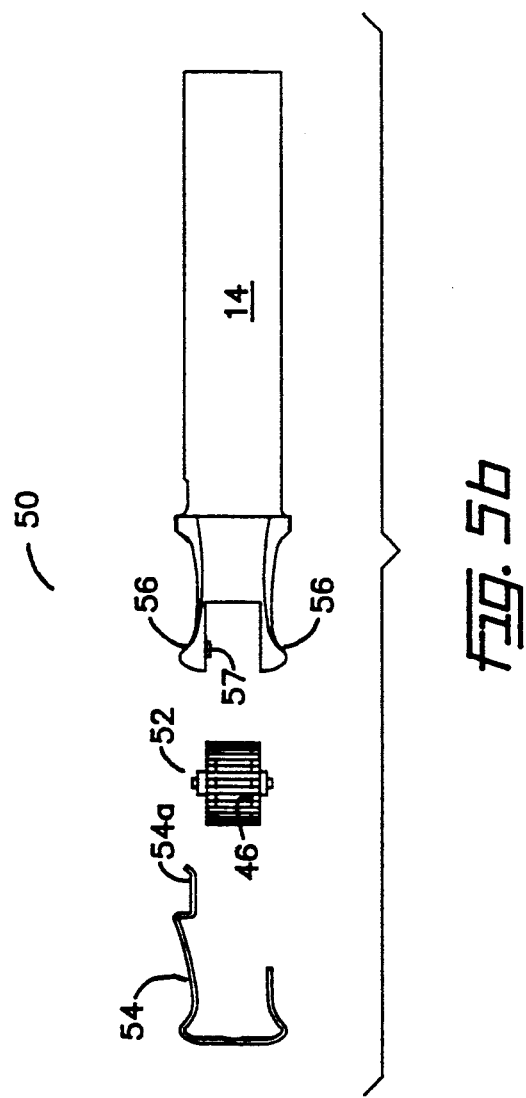
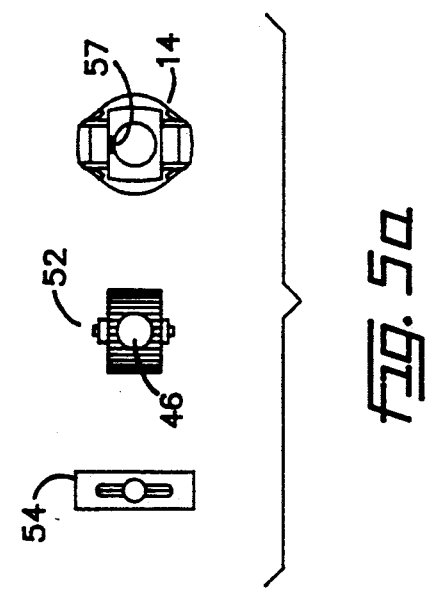
Fig. 5a
Fig. 5b

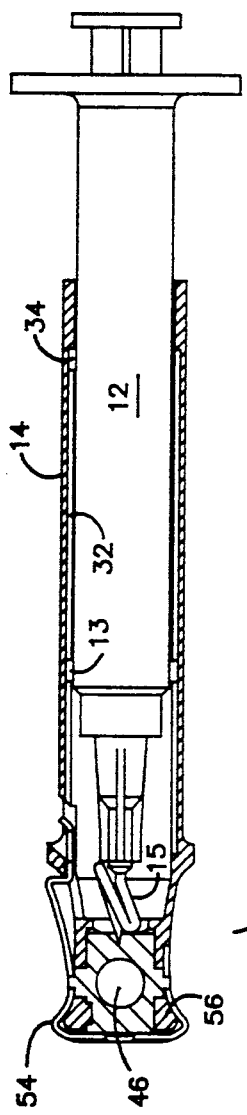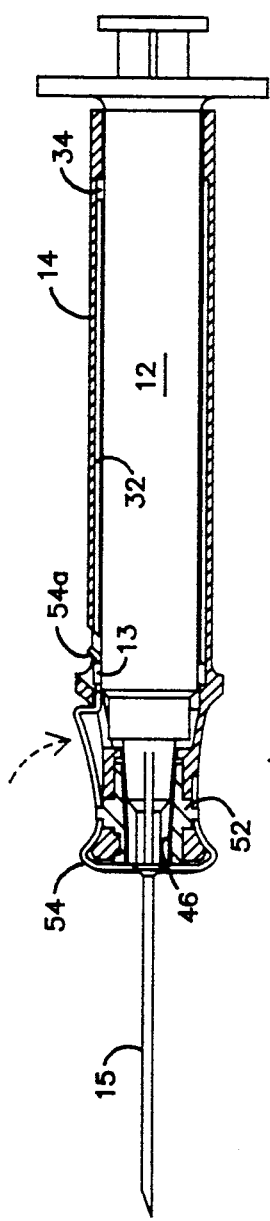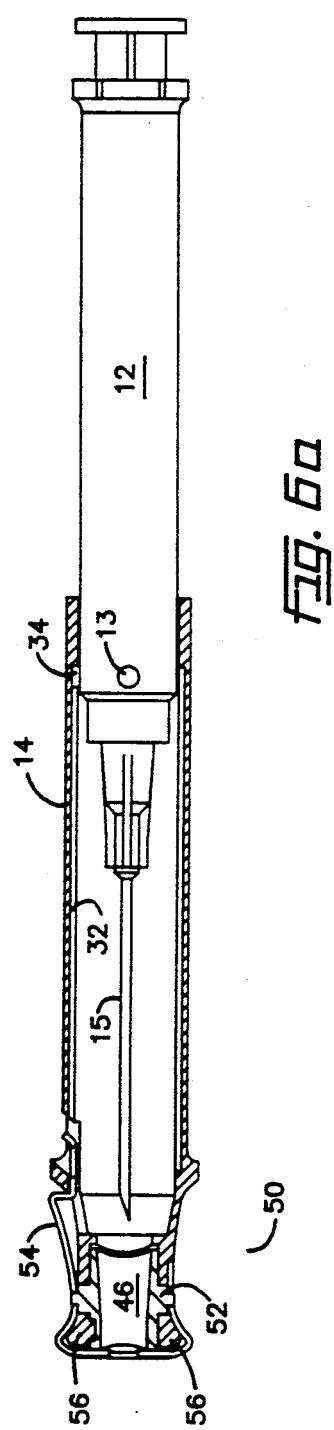

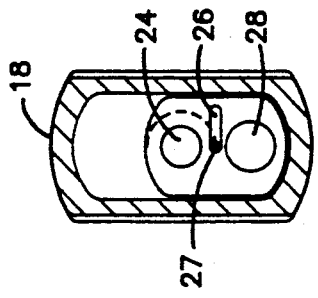
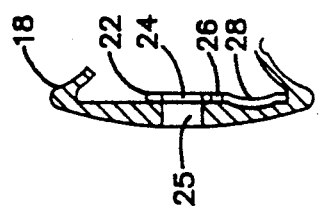
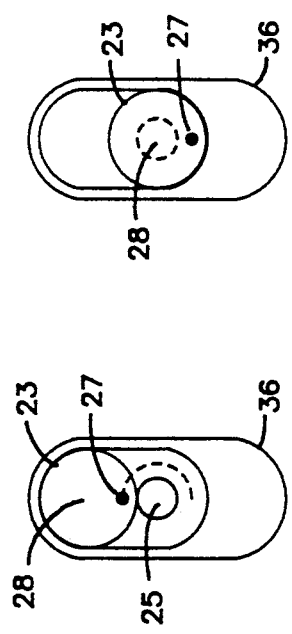
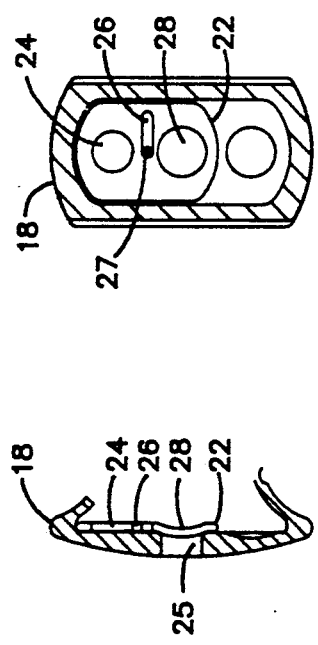

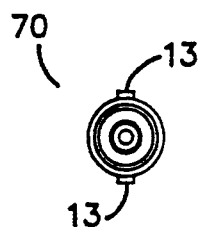 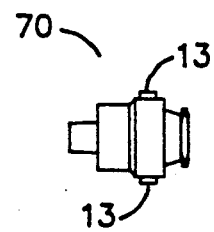 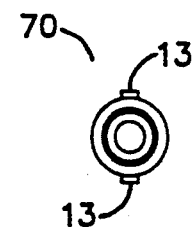
fig. 9a        fig. 9b        fig. 9c
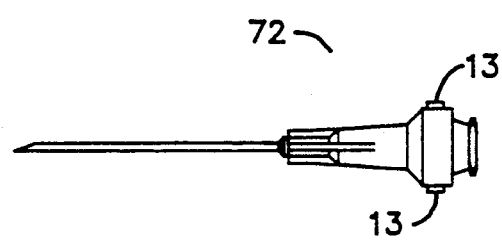 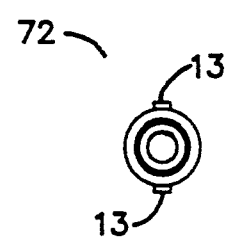
fig. 10a                fig. 10b
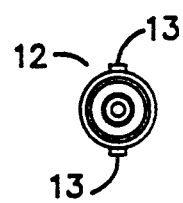 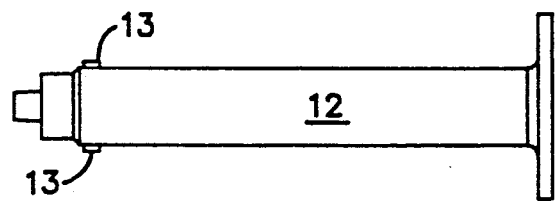
fig. 11a                fig. 11b

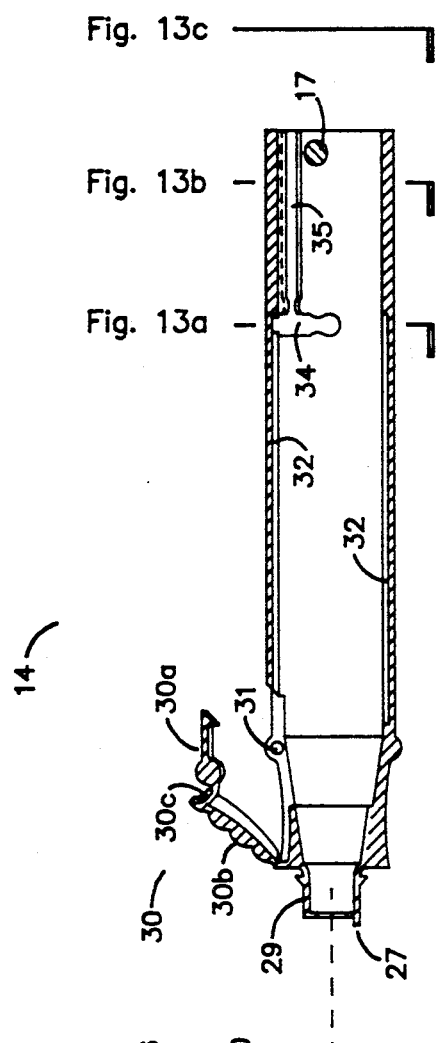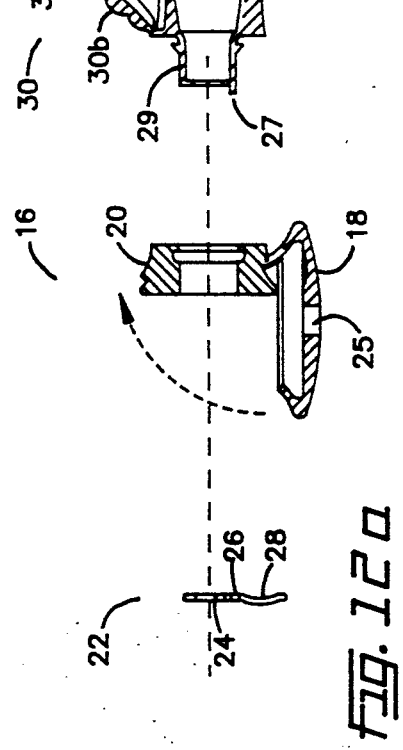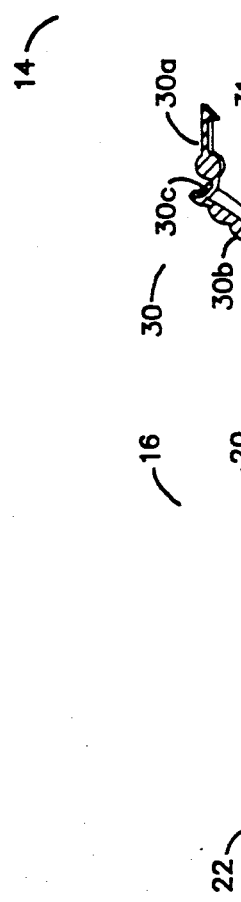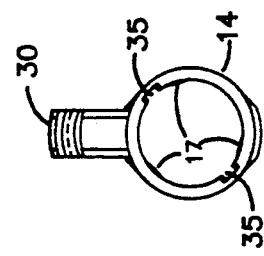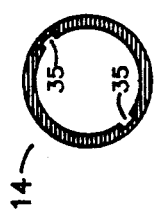

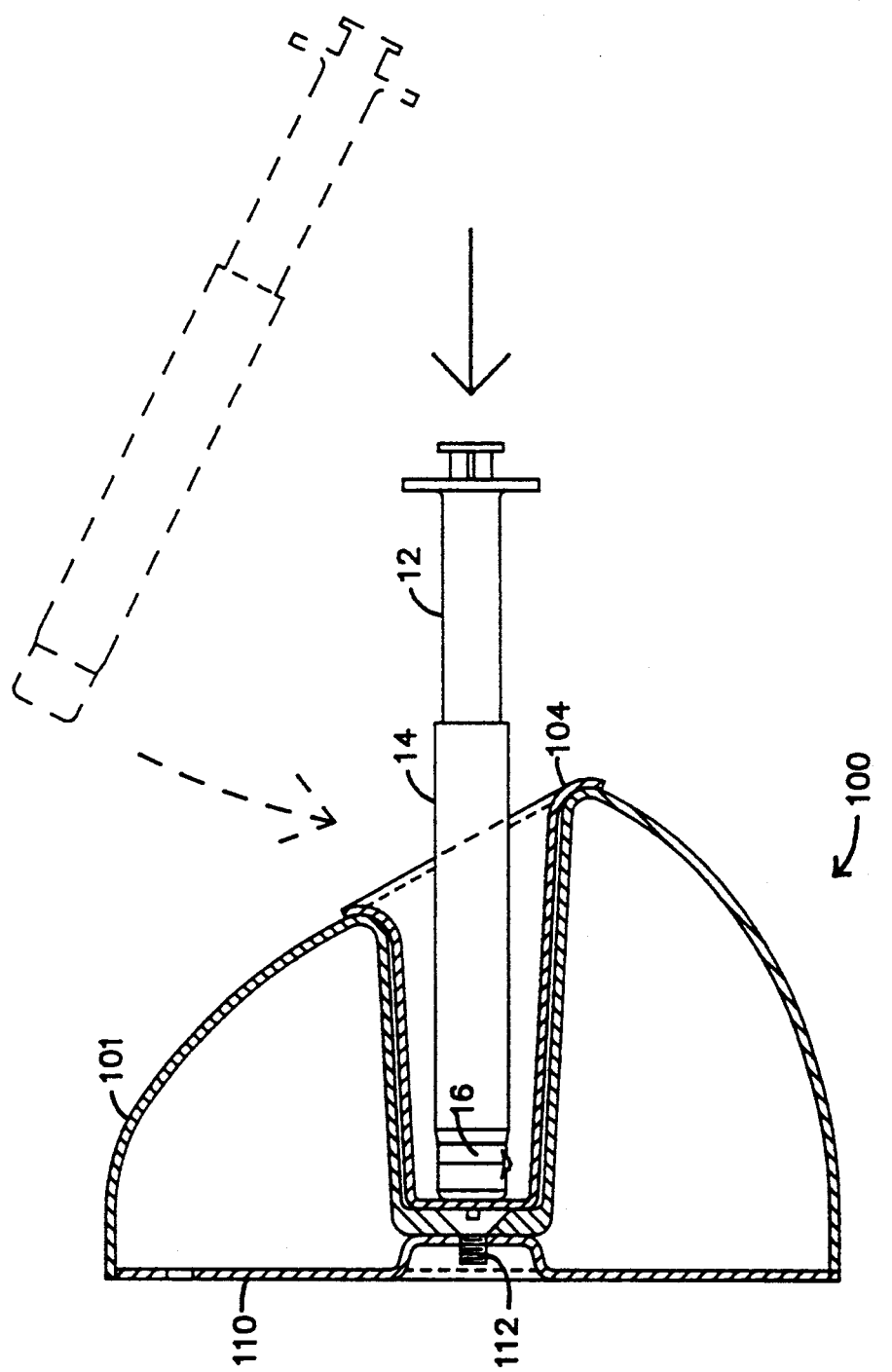

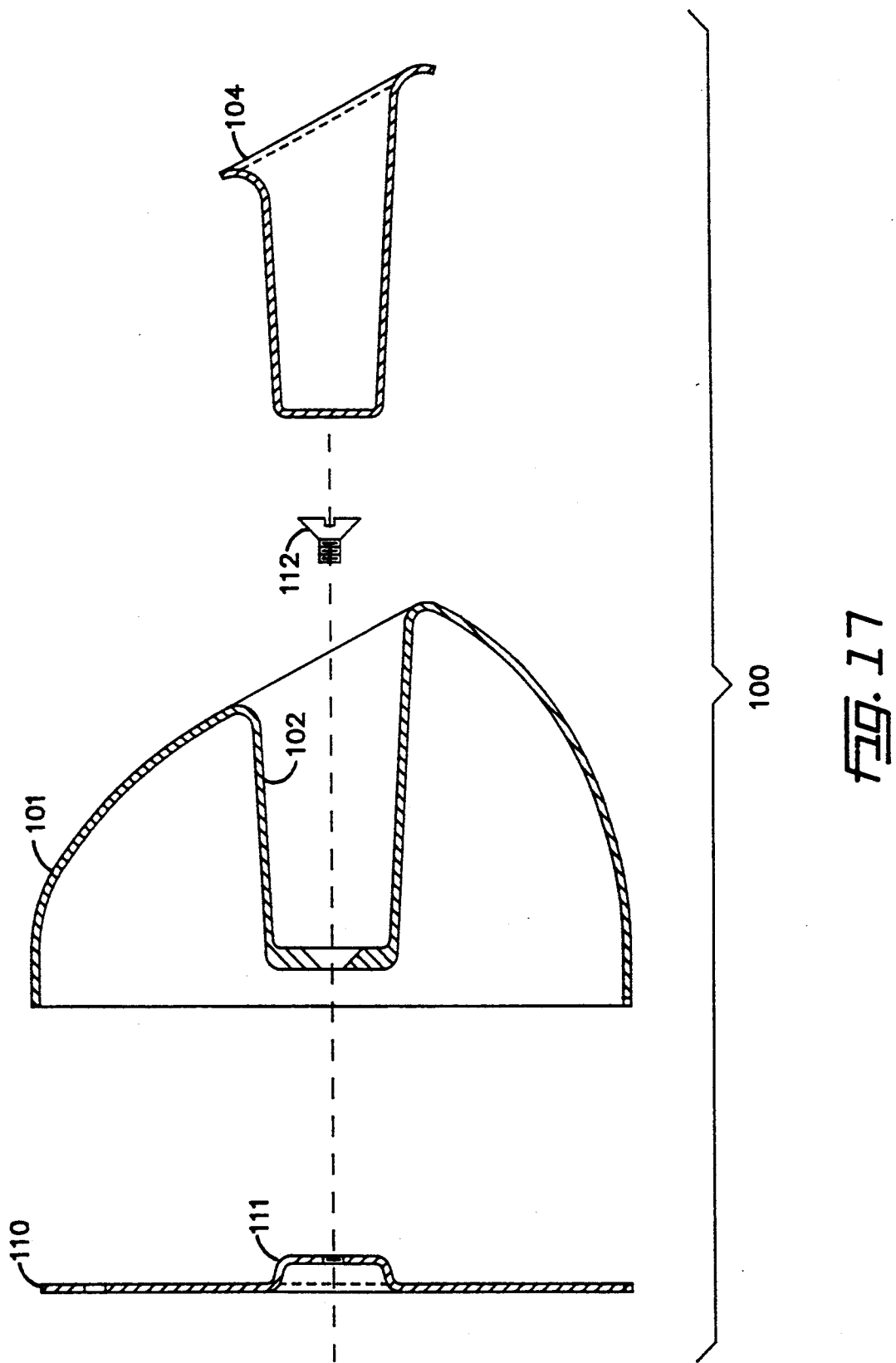

COMBINED PROTECTIVE GUARD AND DESTRUCTION SYSTEM FOR A SYRINGE

CROSS-REFERENCE TO RELATED CASE

This application is a continuation-in-part of an earlier application, U.S. Ser. No. 07/360,585, pending which was filed on June 2, 1989 by the present inventor Robert G. Jullien entitled "Syringe Guard Apparatus".

FIELD OF THE INVENTION

The present invention relates to the field of medical equipment. More specifically, the present invention relates to means for preventing unintended contact of a syringe needle with foreign objects. Particularly, when an injection is to be or has been given to, or a sample withdrawn from, a patient, it is important that the needle does not foul an attendant person or object and perhaps pass bloodborne or other fluidborne pathogens.

BACKGROUND OF THE INVENTION

Discoveries in medical science have long indicated that certain diseases are passed through unintended contact with contaminated needles. Specifically, blood to blood contact, or internal fluid to internal fluid contact, can spread diseases and germs which otherwise cannot be transmitted. To avoid such unintended transmission of pathogens by contaminated needles, particularly for medical professionals, several proposals have been advanced.

The most recent of these proposals has to do with the widely available needle, syringe, and needle cap combination. Specifically, certain governmental agencies are in the process of promulgating guidelines which outline several procedural methods of dealing with the inadvertent spread of infection through contaminated needles. While these procedural suggestions are useful, if they are unobserved, or a participant unavoidably fouls a needle against their person, the disease is none-the-less transmitted.

To address human fallibility with respect to following procedure, several needle guard type apparatus have been suggested. Specifically, guards which telescopically cover the syringe barrel and needle have been proposed. These guards may optionally include latching mechanisms at either end of the guard so as to hold the guard in a particular position with respect to the needle and syringe combination. Further, many of the guards are also proposed as permanent disposal devices for the needle so that if medical waste is improperly disposed of, the risk of a contaminated needle subsequently fouling an individual's person is reduced.

Examples of such prior art guard apparatus can be found in U.S. Pat. Nos. 4,731,059, 4,643,199, 4,425,120, 4,770,655, 4,710,170, 4,728,320, 4,720,738, 4,801,295, and 4,634,428. While these prior art devices provide guards for covering or shielding a needle and syringe combination, they are cumbersome and complex and as such, these devices are not in widespread use.

SUMMARY OF THE INVENTION

It is an object of the present invention to provide a user-friendly and cost efficient apparatus and method for shielding a needle and syringe combination from inadvertent fouling and for destructively crushing the needle once it reaches the end of its useful life, leaving the syringe-needle-guard combination in a safe, sealed condition for ultimate disposal. The guard assembly for use in the apparatus of the present invention optionally includes an easily operated latching mechanism for maintaining the guard in a retracted position in which it surrounds and seals the needle after it has been crushed. Further, the present invention provides a simplified needle disposal technique whereby the needle is positively destroyed and contained within the locked guard and syringe barrel combination. A crush tube is provided for supporting and stabilizing the guard and syringe barrel combination and isolating the assembly during the destruction of the needle. Several embodiments of the present invention may include adapter mechanisms for standard syringe barrels so that the present invention may be used with a stock of existing syringes.

Additional features and advantages of the present invention will become apparent upon the reading of the following description in association with the accompanying drawings.

BRIEF DESCRIPTION OF THE DRAWINGS

FIG. 1a is an isometric view of an embodiment of the guard and syringe assembly according to the present invention;

FIG. 1b is an exploded isometric view of the guard and syringe combination of FIG. 1a;

FIG. 2a is a side view of the combination of FIG. 1, with the guard in its extended position shielding the needle of the syringe;

FIG. 2b is a part-sectional view of the combination shown in FIG. 2a;

FIG. 2c is a part-sectional view of the combination shown in FIG. 1;

FIG. 2d is a part-sectional view of the combination of FIG. 2a, in which the needle has been destructively crushed and sealed within the guard in its retracted position;

FIGS. 4a–4c are part-sectional views of a guard, syringe and needle combination according to the present invention, corresponding to the combination of FIG. 3, showing, respectively, the guard in its extended position, the guard in its retracted position and the guard in its retracted position with the needle having been crushed;

FIGS. 5a and 5b are exploded front and side views, respectively, of a guard assembly including a latching mechanism, for use in the present invention;

FIGS. 6a–6c are part-sectional views of a guard, syringe and needle combination according to the present invention, corresponding to the combination of FIG. 5, showing, respectively, the guard in its extended position, the guard in its retracted position and the guard in its retracted position with the needle having been crushed;

FIGS. 7a and 7b are sectional and end views, respectively, of a sliding plate assembly incorporated in the guard of the assembly of FIG. 1, in which the plate blocks the needle aperture;

FIGS. 7c and 7d correspond to FIGS. 7a and 7b, respectively, showing the plate in its position in which the needle aperture is open;

FIGS. 8a and 8b are end views of an alternative sliding plate assembly for use in the assembly of FIG. 1, in which the needle aperture is, respectively, open and blocked;

FIGS. 9a–9c are, respectively, an end view from one end, side view and end view from the other end of an adaptor for use in the present invention;

FIGS. 10a and 10b are, respectively, side and end views of a combination needle and adaptor for use in the present invention;

FIGS. 11a and 11b are, respectively, end and side views of a syringe barrel for use in the present invention;

FIGS. 12a–12c are together a longitudinal sectional view of an alternative guard assembly for use in the present invention;

FIGS. 13a and 13b are perpendicular sectional views of the guard assembly shown in FIG. 12c along the arrows indicated;

FIG. 13c is an end view of the guard assembly of FIG. 12c along the arrows indicated;

FIG. 15 is a median view of the crush tube and guard and syringe combination of FIG. 14a, showing the movement of the guard and syringe combination as it is placed into the crush tube;

FIG. 17 is an exploded median sectional view of the crush tube shown in FIGS. 14 to 16;

DETAILED DESCRIPTION OF PREFERRED EMBODIMENTS

Figure 3B:
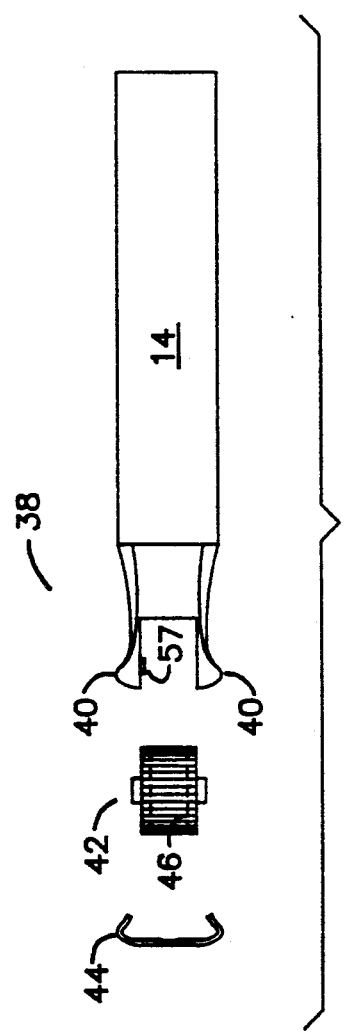
FIGS. 3a and 3b are exploded front and side views, respectively, of a guard and end-piece combination without a latching mechanism, for use in the present invention.

A preferred guard and syringe combination in accordance with the invention is shown in FIGS. 1a and 1b and is designated generally by numeral 10. The guard and syringe combination 10 comprises a syringe barrel 12, a guard 14 and an end-piece 16. The syringe barrel 12 is of a commercially available type, is for example of molded plastic and accommodates a plunger for effecting injection or withdrawal of fluid through the needle 15 which is mounted in the forward end of the syringe barrel 12.

The guard 14 is generally cylindrical and has an open end which telescopes over the forward end of the syringe barrel 12 so as to surround the needle 15. As shown in FIGS. 12 and 13, to aid longitudinal alignment of the syringe barrel 12 within the guard 14, the guard 14 is preferably equipped with interference protrusions 17 which slide along the barrel of the syringe as it is inserted into the guard. This alignment between the guard 14 and syringe barrel 12 ensures accurate alignment of the needle 15 within the guard 14. In the inner wall of the guard 14 are provided slots 35 which engage and guide pins 13 on the outer surface of the syringe barrel 12 into locking slots 34, as will be discussed in detail hereinafter, to lock together the syringe and guard with the guard in its extended position, as shown in FIG. 2b. The inner wall of the guard 14 is further provided with guide slots 32 which engage and guide respective pins 13 as the syringe barrel 12 is slid within the guard 14 into its retracted position.

The end-piece 16 attached to the other end of the guard 14 provides a mechanism for opening or closing an aperture 25 through which the needle 15 passes for use. As shown in FIG. 1, the end-piece 16 comprises a cap 18 and a gripping band 20. Located between the cap 18 and the gripping band 20 is a sliding plate 22 which includes an apertured portion 24 and a solid, impenetrable portion 28. The plate 22 is slidable between two positions, one in which apertured portion 24 is in register with aperture 25 and the other in which solid portion 28 is in register with aperture 25. Thus, sliding of the plate 22 allows a user to selectively open or block off aperture 25 to allow needle 15 to either pass through aperture 25 or to be blocked thereby.

The end-piece 16 is rotatably attached to the end of guard 14 about cylindrical portion 29 which is integral with the guard 14. Cylindrical portion 29 has an aperture passing through its center (unnumbered), which aperture provides a throughway for the needle 15 to pass from the syringe 12. Extending from the forward end of cylindrical portion 29 is pin 27 which engages median slot 26 in sliding plate 22. The relative movement between slot 26 and pin 27 which occurs upon rotation of end-piece 16 with respect to guard 14 causes sliding plate 22 to move from one of its two positions to the other. Thus, selection of the appropriate position of the sliding plate 22 is achieved by relative rotation of end-piece 16 with respect to guard 14, thereby enabling the user to selectively open or block off the needle throughway in a simple manner.

To aid in positively engaging syringe barrel 12 within guard 14, the guard 14 is equipped with latch mechanism 30. In the embodiment shown in FIGS. 1, 2 and 12, the latch is formed as a single molded plastic piece comprising a latch portion 30a and a lever portion 30b. A flexible linking portion 30c connects the latch and lever portions 30a and 30b. The latch portion 30a comprises an end hook for engaging one pin 13 on the outer surface of the syringe barrel 12 when the guard 14 is in its retracted position. The flexible linking portion 30c includes a recessed portion for engagement with one or more latch pins 31 provided on the guard 14 which enable the latch to be secured in its latching position in which it engages the syringe barrel 12 within the guard. The end hook of the latch portion 30a may be raised or lowered so as to disengage or engage pin 13 by exertion of pressure on the lever portion 30b which causes a pivoting action about latch pin(s) 31.

FIG. 2b shows the guard, syringe and needle combination with the guard in its extended position in which it shields the needle 15. This extended position is maintained by securement of pins 13 in respective locking slots 34. In the figure, the sliding plate 22 of end-piece 16 is in its "open" position ready to allow needle 15 to pass therethrough. Of course, when the combination is packaged and transported, the needle aperture will be closed so that the needle 15 is completely enclosed and shielded by the guard 14.

In order to arrive at the condition shown in FIG. 2c from that shown in FIG. 2b, the syringe barrel 12 is first rotated relative to the guard 14 so as to disengage pins 13 from their respective locking slots 34. In the embodiment illustrated this rotation is through an angle of 90 degrees, but any other desired angle may be provided for by appropriate positioning of pins 13 around the perimeter of the syringe barrel 12 and of the locking slots 34 and associated guide slots 35 in the inner wall of the guard 14. With the syringe barrel 12 now free to move telescopically within the guard 14, the two parts are then telescoped together so that the guard 14 assumes its retracted position with needle 15 protruding through aperture 25. During this telescoping movement, the pins 13 are received in and guided by the guide slots 32 in the inner wall of the guard 14. As the guard 14 reaches its retracted position, a pin 13 is pushed past the hook of latch portion 30a and is located in the recess formed behind it. In this manner, unintended withdrawal of the syringe barrel 12 from the guard 14 is prevented by engagement of the pin 13 with the hook of latch portion 30a and intended withdrawal can only be effected by manual operation of the latch mechanism by application of pressure on the lever portion 30b, as has already been described.

After a user has completed use of the syringe, for example for injection or withdrawal of fluid from a patient, the guard and syringe are returned to the position shown in FIG. 2b, in which the guard 14 is in its extended position. The end-piece 16 is rotated relative to guard 14 so as to close needle aperture 25 with the solid portion 28 of sliding plate 22. The whole assembly is then inserted into a crush tube, as will be later described, in order to protect the environment and the user during crushing of the needle. With the forward end of the assembly enclosed within the crush tube, the syringe barrel 12 is telescoped again into the guard 14 by force, so that the forward end of the needle 15 is stopped by closed sliding plate 22 and continued forward pressure on the syringe effects rupture or folding or other collapse of the needle 15 in a destructive manner. Thus, after this destruction the assembly takes the form shown in FIG. 2d, in which the crushed needle can readily be seen to be completely shielded and enclosed within the guard and syringe combination.

Figure 3C:
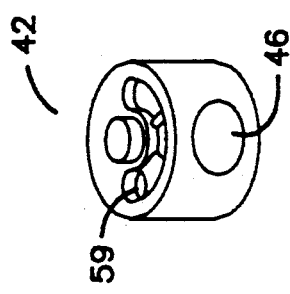
FIG. 3c is a perspective view of the thumb wheel as used in the combination of FIGS. 3a and 3b.
Figure 3A:
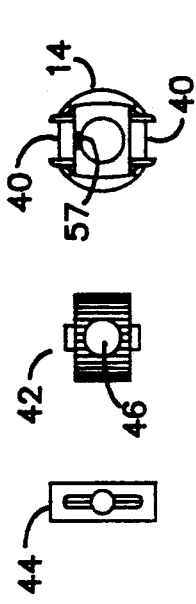

FIGS. 3a-3c show part of an alternative form of guard for use in the present invention. Here, the guard 14 and end-piece 38 are integrally formed, and end-piece 38 includes stirrups 40. Stirrups 40 extend forwardly of guard 14 and lie to either side of a knurled thumb wheel 42. Thumb wheel 42 has an aperture 46 formed therein, and is selectively rotatable into any one of three positions: a first position wherein aperture 46 is aligned with the needle 15 extending from the syringe barrel 12, a second position wherein the aperture 46 is non-aligned with, e.g. transverse to, the direction of the needle 15 and a third position wherein the aperture 46 is again non-aligned with, e.g. transverse to, the direction of the needle 15 but wherein the thumb-wheel is permanently locked in that third position. The locking mechanism for the thumb-wheel in the third position is illustrated in FIG. 3c, which shows the thumb-wheel 42 in isometric view. As shown, thumb-wheel 42 includes a locking aperture 59 which permanently engages locking pin 57 on one stirrup 40 when the thumb-wheel is in its third position. Rotation of the thumb-wheel 42 from the second position brings the thumb-wheel firstly into its first position in which the aperture 46 is aligned with the direction of the needle 15 to allow passage of the needle through the end-piece 38, and further rotation in the same direction brings the thumb-wheel 42 into its third position in which it permanently blocks off the needle throughway. Thus, in this manner the rotatable thumb-wheel 42 enables a user to selectively prevent [temporarily or permanently] or allow passage of the needle 15 through the end-piece 38. The sequence of operations for achieving this is illustrated in FIGS. 4a-4c, as will now be described.

FIG. 4a shows a syringe 12 installed in guard 14 including end-piece 38 and thumb-wheel 42. The aperture 46 in the thumb-wheel 42 is aligned with the needle 15, so that the latter can pass through the end-piece as the syringe barrel 12 is telescopically moved through guard 14. As seen in FIG. 4a, there is further provided an end clip 44 for holding the thumb-wheel 42 in place in the end-piece 38. The end clip 44 has a central aperture therein, to allow the needle 15 to pass through it when necessary. The end cap 44 is made of a resilient material, e.g. plastic, so that it can simply be clipped into place over the outer surfaces of stirrups 40 as shown in the Figure.

From the condition shown in FIG. 4a, the syringe barrel 12 is rotated to align pins 13 with slots 32 and is moved through guard 14 in the same manner as before, until the needle hub reaches its limiting position in abutment with the forward end of the guard 14 and/or with the thumb-wheel 42. Since in this embodiment there is no latch mechanism 30 for holding the guard 14 in its retracted position with respect to the syringe barrel 12, the forward end of the needle hub of the syringe is preferably dimensioned so as to be insertable at least part of the way into the aperture 46 of the thumb-wheel 42. This allows the needle hub, and thus the syringe barrel 12 to which it is attached, to be held in the position shown in FIG. 4b by means of friction between the needle hub and the inner wall of the aperture 46.

Once use of the syringe is completed the syringe barrel 12 can simply be pulled from the retracted position shown in FIG. 4b to the extended position shown in FIG. 4a. The thumb-wheel 42 is then rotated into its third position in which it is locked by engagement of locking aperture 59 with locking pin 57 and the needle aperture in the end-piece 38 blocked off. As before, the syringe barrel 12 is then forcibly pushed back into the guard 14 towards the retracted position, while the whole assembly is protected within a crush tube, as will be described later. As the tip of the needle 15 is forced against the solid surface of the thumb-wheel 42, the needle is destructively crushed as before, the final position of the syringe barrel 12 and guard 14 being substantially as shown in FIG. 4c.

FIGS. 5a and 5b illustrate an alternative embodiment of the thumb-wheel assembly shown in FIG. 3. Here, the end-piece 50 includes stirrups 56, thumb-wheel 52 [substantially the same as thumb-wheel 42 of FIG. 3] and latch 54. The latch 54 also serves as an end cap which may be clipped over the stirrups 56 to secure the thumb-wheel assembly together. A portion 54a of the latch 54 has an aperture formed therein and this portion forms a clip for releasable engagement with a pin 13 on the outer surface of the syringe barrel 12 inserted into the guard 14, in a similar manner to the hooked portion 30a of the latch shown in FIG. 12. The action of this latching mechanism is illustrated further in FIGS. 6a-6c, which correspond to FIGS. 4a-4c of the first embodiment of the thumb-wheel assembly. As shown in FIG. 6b, in order to disengage the latch 54 from pin 13 for the purpose of moving the syringe barrel combination to the extended position, downward pressure

[shown by the arrow] is applied to the lever portion of the latch 54, thereby causing a pivoting action about the central pivoting portion of the latch which forces portion 54a of the latch upwardly into its non-retaining position with respect to pin 13.

FIGS. 7a-7d show a sliding plate assembly for use in the invention, which has already been partly described with reference to FIGS. 1 and 2. The assembly comprises end cap 18 and sliding plate 22. The plate 22 includes a median slot 26 which engages actuating pin 27 integral with cylindrical portion 29 of the forward end of the guard 14 [see FIG. 1]. FIGS. 7a and 7b illustrate the plate 22 in a first position in which solid, impenetrable portion 28 of the plate 22 obscures aperture 25 in the end cap 18. As shown in FIG. 7a, the solid portion 28 of the plate 22 may be arcuate so as to partially protrude into the aperture 25. This can help to maintain the plate in this first position and guard against accidental release of the plate 22 out of its blocking position. Upon relative rotation of the end cap 18 with respect to guard 14, the pin 27 slides within slot 26 and as it does so urges against the lower side of the slot as shown in FIG. 7b, thereby urging the plate 22 from the position shown in FIG. 7b into the position shown in FIG. 7d. Now the apertured portion 24 of plate 22 is aligned with aperture 25 in the end cap 18, enabling the needle 15 to pass therethrough as the guard 14 is moved telescopically with respect to the syringe barrel 12 into its retracted position.

When a user has determined that the time has come for the syringe and needle combination to be disposed of, the end cap 18 is rotated in the reverse direction with respect to guard 14 in order to return the plate 22 to its blocking position as shown in FIG. 7b. At this point, therefore, the needle 15 will be fully enclosed within the assembly. Next, rotation of the end cap 18 is continued in the same direction past the point necessary to return plate 22 to its blocking position, so that pin 27 is sheared and no longer able to transmit movement to plate 22 via slot 26. Hence, plate 22 is now disabled and in a permanent blocking position. Forcible telescopic movement of the syringe barrel 12 with respect to the guard 14 can now be effected as before, with the forward portion of the assembly protected within a crush tube, as described in detail below, thereby destructively crushing the needle against the solid, impenetrable portion 28 of plate 22.

FIGS. 8a and 8b show an alternative form of sliding plate assembly, in which the sliding plate 23 is circular and slides within a round-ended elongate recess in the end cap 36 between an open position, as shown in FIG. 8a, and a closed position, as shown in FIG. 8b. As before, movement of plate 23 between the two positions is governed by pin 27 which engages the plate 23 by means of a hole provided therein. In this embodiment, as the end cap 36 is rotated relative to the guard 14, motion of the pin 27 causes plate 23 to rotate and slide within its recess. As before, when the time comes for the plate 23 to be disabled and locked permanently in its closed position, the end cap 36 is rotated to the position shown in FIG. 8b. Further rotation of end cap 36 in either direction will cause plate 23 to spin while maintaining its position over aperture 25. Thus, aperture 25 is permanently blocked.

In the above described moving plate assemblies, at least the blocking portions 28 of the respective sliding plates 22 are formed of a hard, impenetrable material, e.g. a hard plastic.

FIG. 9 shows an adapter for use with existing syringe barrels, so that existing stock can be used with a guard in accordance with the present invention. The adapter 70 fits between an existing syringe barrel and needle hub and pins 13 provided on the outer surface of the adapter 70 enable the adapter-conventional syringe barrel combination to function in the same way as the syringe barrel 12 as described hereinbefore.

FIG. 10 shows a needle adapter 72 equipped with guide pins 13 which may be used as an alternative to the adapter shown in FIG. 9 for enabling a conventional syringe barrel to be used with the guard of the present invention. FIG. 11 illustrates a syringe barrel 12 which may be fitted with a conventional needle hub for use in the present invention.

FIG. 12, which has already been described, is an exploded sectional view of the guard 14 of the assembly shown in FIG. 1. This Figure shows the pivoting and connecting relationships between the respective endpiece members and also shows in detail the preferred latch mechanism 30.

FIG. 13 shows various views of the guard of FIG. 12 along the arrows indicated in that Figure. In particular, FIG. 13a shows a preferred positioning of locking slots 34 and their relationship to guide slots 32, FIG. 13b shows a preferred location of syringe removal slots 35 and FIG. 13c shows an end view of the guard 14.

Figure 14A:
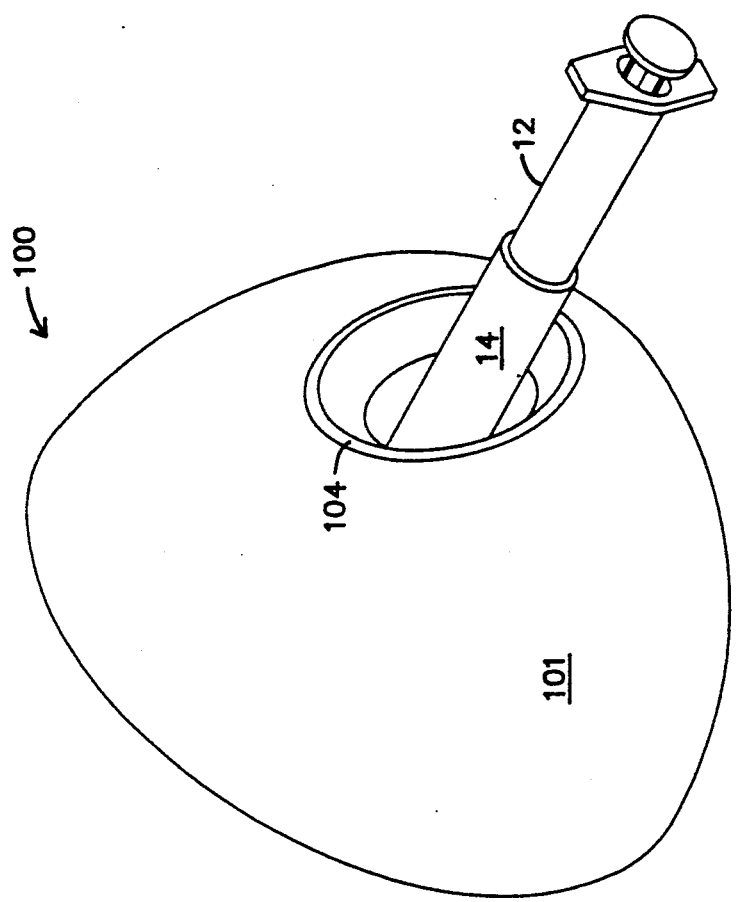
FIGS. 14a and 14b are isometric views of a preferred crush tube for use in the present invention, showing the guard and syringe combination respectively before and after crushing of the needle.
Figure 14B:
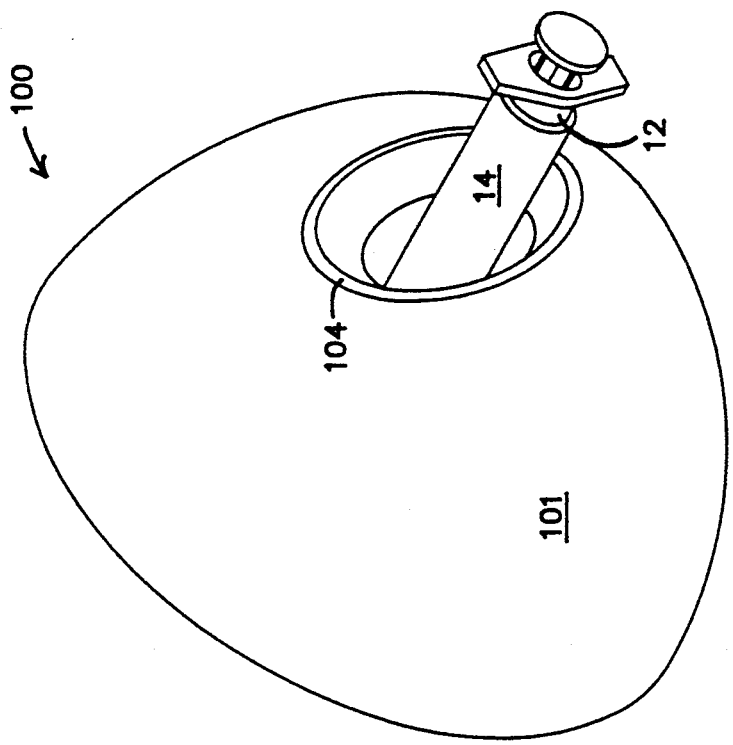
Figure 16A:
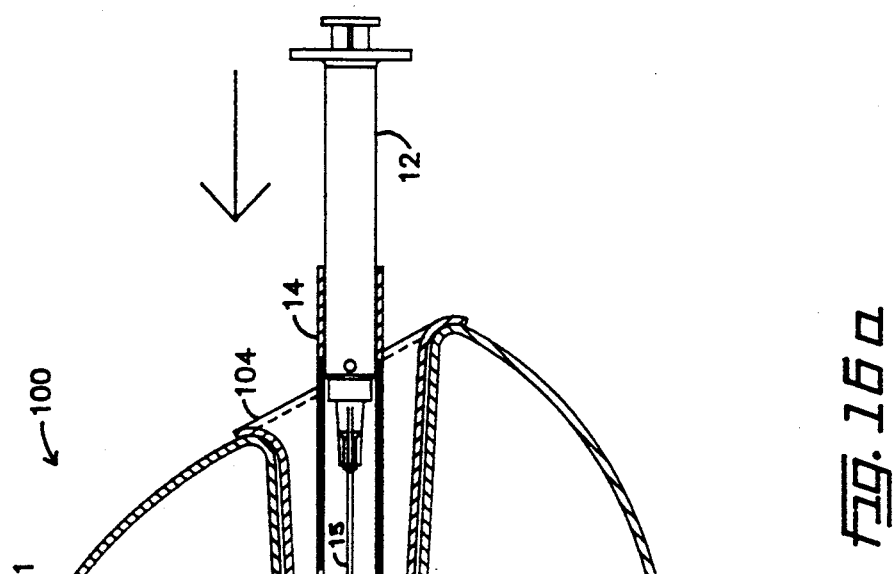
FIGS. 16a and 16b are part-sectional views of the crush tube and guard and syringe combination of FIGS. 14a and 14b, respectively.
Figure 16B:
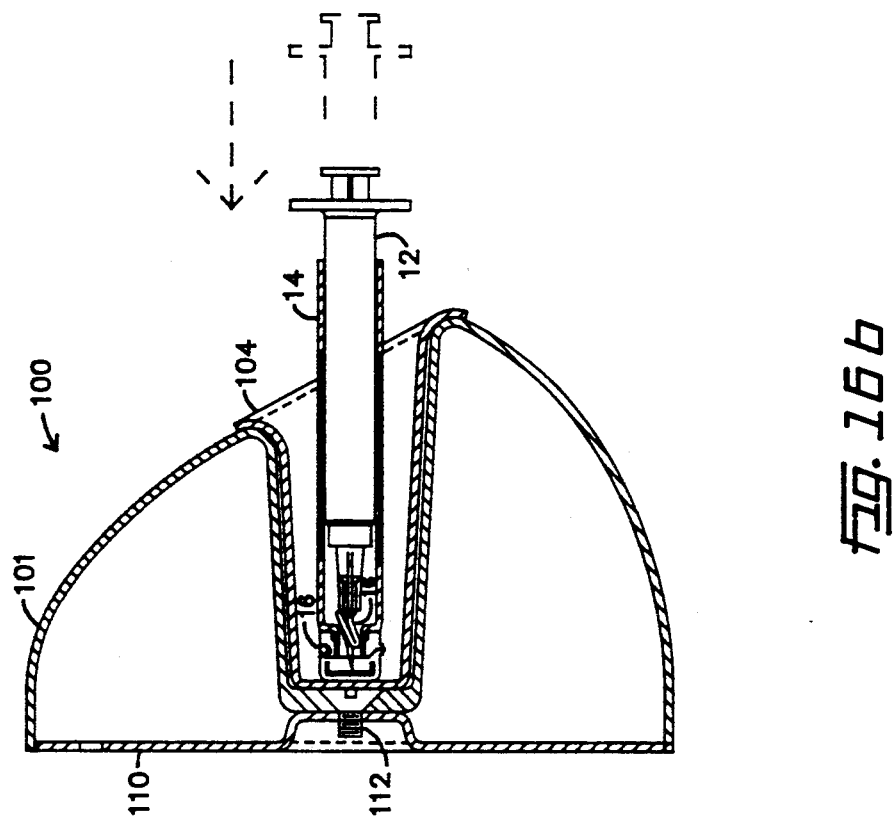

FIGS. 14a and 14b show isometric views of a preferred crush tube 100 into which a guard-syringe assembly has been placed, respectively prior to and after destruction of the needle 15. These same views are shown in cross-section in FIGS. 16a and 16b, respectively. After the guard 14 has been returned to its extended position with respect to the syringe barrel 12 and the needle aperture 25 in the forward end of the assembly closed, the assembly is placed into the crush tube 100 via its open end, as shown in FIG. 15 (the dashed lines in that Figure representing the movement of the assembly as it is placed into the crush tube). As force is applied to the syringe barrel 12 in the direction of the solid arrows in FIGS. 15 and 16a, movement of the guard 14 is resisted by the closed end of the crush tube 100, thereby causing the needle 15 to fold or rupture and thereby to be destructively crushed. The final, crushed condition is illustrated in FIG. 16b.

As shown in clearer detail in FIG. 17, the preferred crush tube 100 comprises a generally hemispherical, unitary shell 101, e.g. of hard plastic or metal, having a tubular, re-entrant portion 102 near its center. The re-entrant portion 102 is preferably cylindrical or slightly frusto-conical in shape, the latter assisting location of the end of the guard-syringe assembly therein, as shown in FIG. 15. The shell 101 is secured, preferably detachably, to a base plate 110, for example by screw 112 or other suitable means, in order to provide a rigid support for the crush tube and which will bear on or against and protect a fixed surface such as a table-top or wall during the needle destruction procedure. The base plate 110, seen in clearer detail in FIGS. 20a and 20b, is preferably provided with a raised portion 111, behind which the threaded end portion of screw 112 or other fixing means is accommodated, so as to maintain the substantially planar rear support surface of the base plate 110.

The crush tube 100 preferably includes a liner 104 to isolate the crush tube from possible contaminants. The liner 104 may be semi-permanent, i.e. intended for disposal after the needles of several syringes have been crushed, or may be designed for one-off use only. The liner 104 may be formed of any suitable material which is physically and/or chemically resistant to substances which may be present in the syringes with which the crush tube is to be used. In the form of liner shown in FIG. 17, the liner 104 is semi-rigid and substantially conforms to the shape of the re-entrant portion 102 of the shell 101. Alternatively, the liner may be flexible, so that if desired a spent guard-syringe assembly can be securely sealed within the liner for safe and easy disposal as a unitary package.

Figure 18:
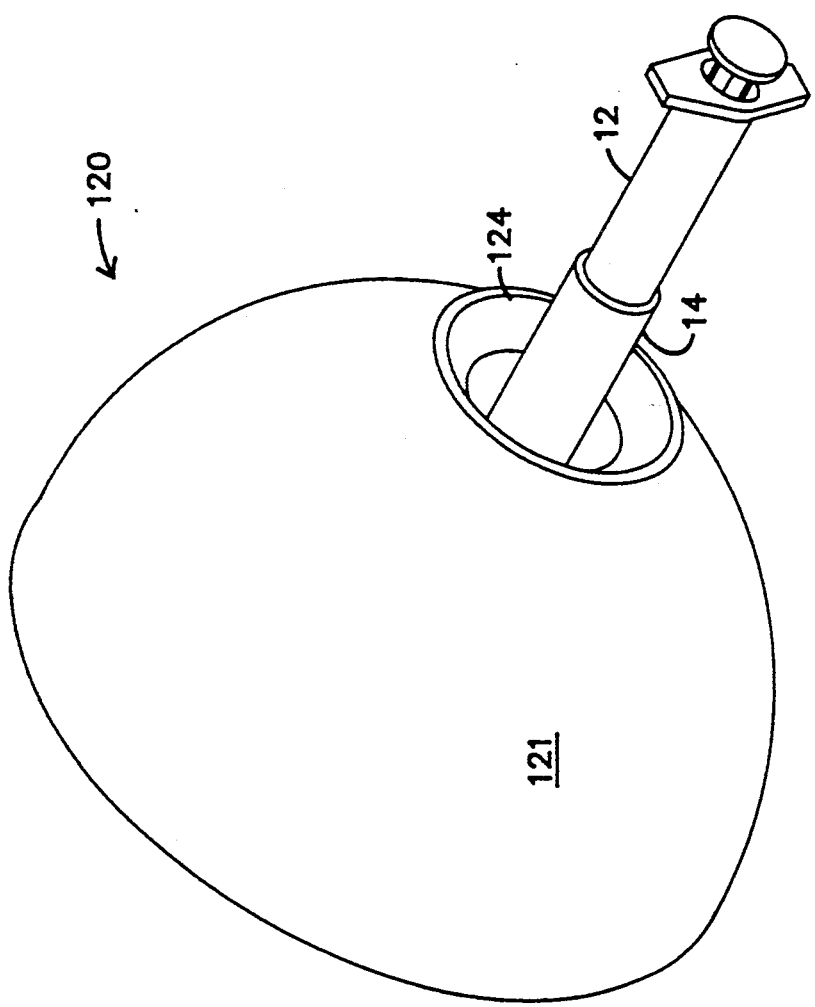
FIG. 18 is an isometric view of an alternative crush tube for use in the invention, showing the guard and syringe combination before crushing of the needle.
Figure 19:
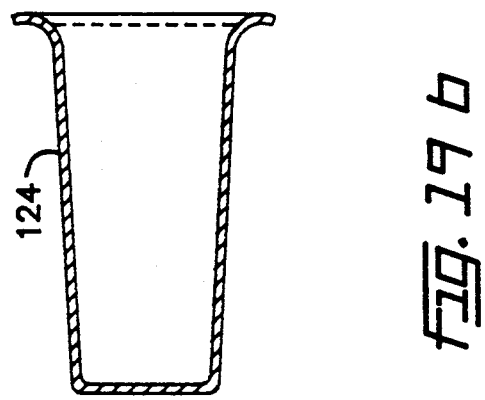
FIGS. 19a and 19b are together an exploded part-sectional view of the alternative crush tube shown in FIG. 18.
Figure 19:
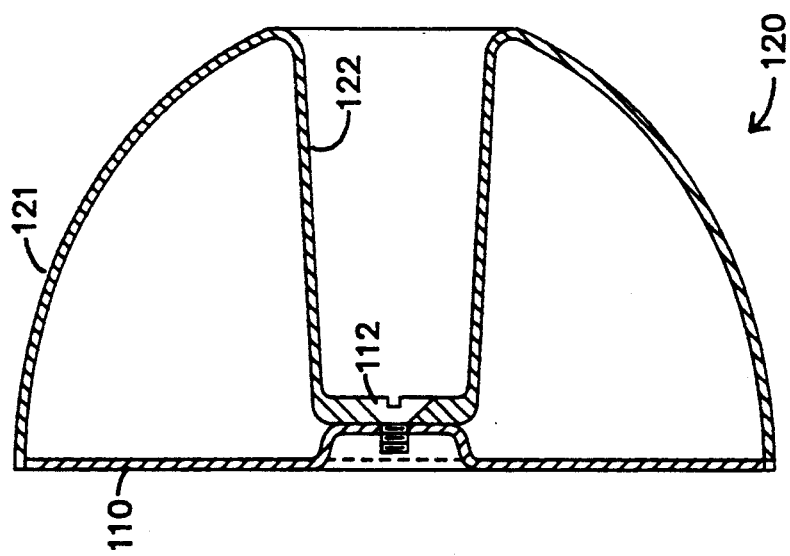

The shell 101 of the crush tube 100 shown in FIGS. 14 to 17 is a spherically asymmetrical embodiment, in the sense that the curvature of the shell 101 varies angularly about its axis, which is generally the same as the axis of the tubular re-entrant portion 102 thereof. FIG. 18 illustrates an alternative crush tube 120 in which the shell 121, its re-entrant portion 122 and the liner 124 are spherically symmetrical. This embodiment is shown in clearer detail in FIGS. 19a and 19b.

Figure 20B:
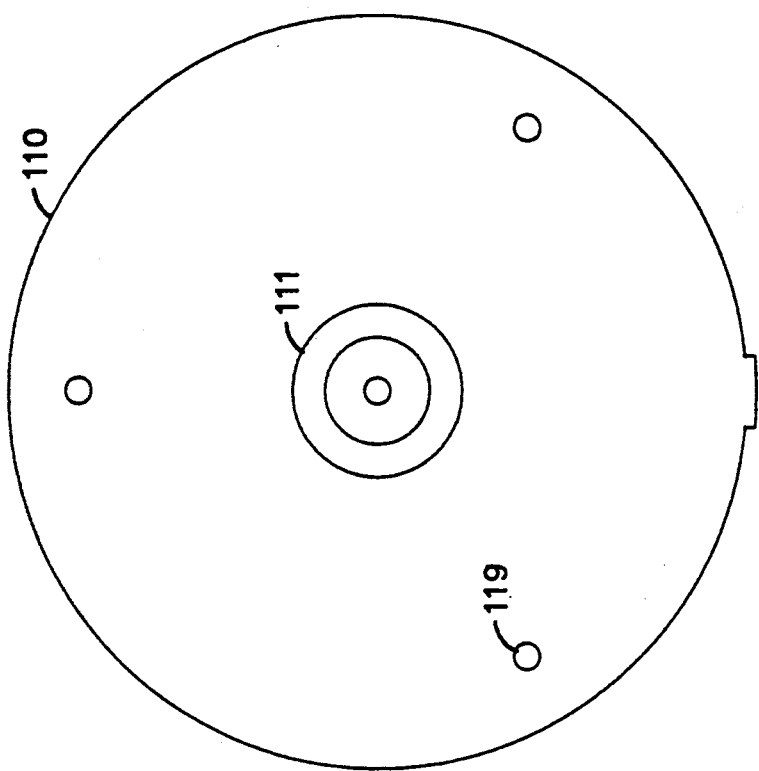
FIGS. 20a and 20b are side and face views, respectively, of the base plate of the crush tubes shown in FIGS. 14 to 19.
Figure 20A:
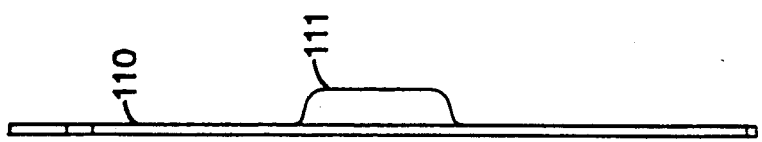

FIGS. 20a and 20b illustrate the preferred base plate 110 used in the crush tubes shown in FIGS. 14 to 19. If desired, the base plate 110 may include apertures 119 for enabling the plate 110 to be permanently affixed to a support surface, e.g. a table-top, wall or a work surface, which is to support the crush tube and guard-syringe assembly during the needle crushing procedure. Thus, the crush tube of the invention may form a syringe-crushing station which is either fixed or portable.

What is claimed is:

1. In combination:
   [i] an assembly for injecting fluid into or drawing fluid from a substrate, said assembly comprising:
      a barrel for containing said fluid to be injected into or drawn from said substrate, said barrel having a needle mounted at one end thereof for transferring said fluid between said barrel and said substrate;
      a tubular guard having first and second ends, said guard being adapted for telescopically receiving said needle and at least a portion of said barrel via said second end, said barrel being telescopically slidable within said guard between an extended position in which said one end of said barrel is proximal said second end of said guard and said needle is contained within said guard and a retracted position in which said one end of said barrel is proximal said first end of said guard; and
      an end-piece mounted on said first end of said guard, said end-piece including means for selectively opening or closing an aperture in said end-piece for selectively allowing passage of said needle through said end-piece as said barrel is slid within said guard from said extended position to said retracted position,
      wherein said needle is destructively crushed upon sliding said barrel from said extended position to said retracted position when said aperture in said end-piece is closed; and
   [ii] a tubular receptacle for receiving via an open end thereof at least a portion of said assembly proximal said first end of said guard, said receptacle having a closed end opposite said open end for limiting movement of said guard as said barrel is slid from said extended position to said retracted position during said destructive crushing of said needle.

2. In combination as in claim 1, wherein said means for selectively opening or closing said aperture in said end-piece comprises a thumb-wheel rotatable about a rotational axis transverse to a longitudinal axis of said needle, said thumb-wheel having an aperture therethrough transverse to said rotational axis, said thumb-wheel being rotatable about said rotational axis between a first position in which said aperture is aligned with said needle for allowing said passage of said needle through said end-piece, and a second position in which said aperture is non-aligned with said needle for blocking said passage of said needle through said end-piece.

3. In combination as in claim 2, wherein said thumb-wheel is rotatably mounted on stirrups extending from said first end of said guard.

4. In combination as in claim 2, wherein said thumb-wheel is further rotatable about said rotational axis into a permanently lockable third position in which said aperture is non-aligned with said needle so as to permanently block said passage of said needle through said end-piece.

5. In combination as in claim 1, wherein said means for selectively opening or closing said aperture in said end-piece comprises a slidable plate having an apertured portion and a solid portion, said plate being slidable in said end-piece between a first position in which said apertured portion is aligned with said needle for allowing said passage of said needle through said end-piece, and a second position in which said solid portion is aligned with said needle for blocking said passage of said needle through said end-piece.

6. In combination as in claim 5, wherein said end-piece is rotatable relative to said guard and said means for selectively opening or closing said aperture further comprises a pin attached to said guard and engaging a slot in said slidable plate, whereby rotation of said end-piece relative to said guard causes sliding of said plate between said first and second positions.

7. In combination as in claim 1, further comprising a latch for selectively locking said guard and said barrel in said retracted position.

8. In combination as in claim 1, further comprising releasable locking means for selectively locking said guard and said barrel in said extended position.

9. In combination as in claim 8, wherein said locking means comprises one or more pips on the outer surface of said barrel which engage one or more respective locking slots provided in said guard means.

10. In combination as in claim 1, wherein said tubular receptacle further comprises a disposable liner.

11. In combination as in claim 1, wherein said tubular receptacle is a re-entrant portion of a shell, said shell being secured to a base plate which bears against a fixed surface during said crushing of said needle.

12. In combination as in claim 11, wherein said shell is detachably affixed to said base plate.

13. A method of destructively crushing a needle of an assembly for injecting fluid into or drawing fluid from a substrate, said assembly comprising:
   a barrel for containing said fluid and having said needle mounted at one end thereof for transferring said fluid between said barrel and said substrate;
   a tubular guard having first and second ends, said guard being adapted for telescopically receiving said needle and at least a portion of said barrel via said second end, said barrel being telescopically slidable within said guard between an extended position in which said one end of said barrel is proximal said second end of said guard and said needle is contained within said guard and a retracted position in which said one end of said barrel is proximal said first end of said guard; and an end-piece mounted on said first end of said guard, said end-piece including means for selectively opening or closing an aperture in said end-piece for selectively allowing or blocking passage of said needle through said end-piece as said barrel is slid within said guard from said extended position to said retracted position, said method comprising:
[i] taking said assembly with said barrel in said extended position and said aperture in said end-piece closed so as to block said passage of said needle through said end-piece and placing at least a portion of said assembly proximal said first end of said guard into a tubular receptacle via an open end thereof, said receptacle having a closed end opposite said open end for limiting movement of said assembly as said barrel is slid from said extended position to said retracted position; and

[ii] forcibly sliding said barrel from said extended position to said retracted position so as to destructively crush said needle against said end-piece.

14. A method as in claim 13, wherein said tubular receptacle further comprises a disposable liner and said method further includes after step ]ii] the step of disposing of said liner with said assembly containing said crushed needle therewithin.

15. A method as in claim 13, wherein said tubular receptacle is a re-entrant portion of a shell, said shell being secured to a base plate, and said method includes between steps ]i] and ]ii] the step of placing said base plate on or against a fixed surface, so that said base plate bears against said fixed surface during said crushing of said needle.

* * * * *